US009554912B2

(12) United States Patent
Goodfellow et al.

(10) Patent No.: US 9,554,912 B2
(45) Date of Patent: Jan. 31, 2017

(54) TIBIAL PROSTHETIC COMPONENT FOR A PARTIAL OR UNICONDYLAR BEARING KNEE REPLACEMENT, METHOD OF SELECTING SUCH A TIBIAL PROSTHETIC COMPONENT, METHOD OF IMPLANTING SUCH A TIBIAL PROSTHETIC COMPONENT AND A KIT FOR A SURGEON

(71) Applicant: BIOMET LTD, Bridgend, South Wales (GB)

(72) Inventors: John Goodfellow, Oxford (GB); John O'Connor, Oxford (GB); Chris Dodd, Oxford (GB); David Murray, Oxford (GB)

(*) Notice: Subject to any disclaimer, the term of this patent is extended or adjusted under 35 U.S.C. 154(b) by 0 days.

(21) Appl. No.: 14/535,542

(22) Filed: Nov. 7, 2014

(65) Prior Publication Data
US 2015/0134069 A1  May 14, 2015

Related U.S. Application Data

(63) Continuation of application No. 13/583,902, filed as application No. PCT/GB2011/050486 on Mar. 11, 2011, now Pat. No. 8,906,106.

(30) Foreign Application Priority Data

Mar. 11, 2010  (GB) .................................. 1004068.1

(51) Int. Cl.
*A61F 2/38*  (2006.01)
*A61F 2/46*  (2006.01)
*A61F 2/30*  (2006.01)

(52) U.S. Cl.
CPC .............. *A61F 2/389* (2013.01); *A61F 2/4684* (2013.01); *A61F 2002/30168* (2013.01);
(Continued)

(58) Field of Classification Search
CPC ........... A61F 2/389; A61F 2/38; A61F 2/3868
See application file for complete search history.

(56) References Cited

U.S. PATENT DOCUMENTS

| 4,714,474 A | 12/1987 | Brooks, Jr. et al. |
| 5,246,459 A | 9/1993 | Elias |

(Continued)

FOREIGN PATENT DOCUMENTS

| EP | 1693026 A | 8/2006 |
| GB | 2312168 A | 10/1997 |

(Continued)

OTHER PUBLICATIONS

UK IPO Search Report dated Jun. 28, 2010 in connection with GB Patent Application No. 1004068.1, 5 pages.
(Continued)

*Primary Examiner* — Jason-Dennis Stewart
(74) *Attorney, Agent, or Firm* — Schwegman, Lundberg & Woessner, P.A.

(57) ABSTRACT

The invention concerns a tibial prosthetic component comprising a plate (100) for forming a tibial plateau of a tibia (16), wherein a peripheral region of the plate (100) has a thickness of less than 3 mm. The invention also concerns a tibial prosthetic component having a keel of depth less than 9 mm. The invention also concerns a method of selecting a tibial prosthetic component comprising receiving measurements of at least one physical attribute of an individual into whom the tibial prosthetic component is to be implanted, selecting a thickness of a plate (100) and depth of keel of the tibial prosthetic component based on the measurements and providing a tibial prosthetic component comprising a plate (100) having the selected thickness and a keel having the selected depth. The invention may also comprise implanting a tibial prosthetic component selected in accordance with this method into an individual and a kit comprising a
(Continued)

plurality of prosthetic components comprising plates having different thicknesses with keels of different depths.

17 Claims, 10 Drawing Sheets

(52) U.S. Cl.
CPC ............... *A61F 2002/30594* (2013.01); *A61F 2002/30616* (2013.01); *A61F 2002/30878* (2013.01); *A61F 2002/30884* (2013.01); *A61F 2002/30901* (2013.01); *A61F 2002/3895* (2013.01)

(56) References Cited

U.S. PATENT DOCUMENTS

| | | | |
|---|---|---|---|
| 6,258,127 | B1 | 7/2001 | Schmotzer |
| 8,906,106 | B2 | 12/2014 | Goodfellow et al. |
| 2003/0060884 | A1 | 3/2003 | Fell et al. |
| 2004/0006393 | A1 | 1/2004 | Burkinshaw |
| 2004/0153163 | A1 | 8/2004 | Posner |
| 2005/0049524 | A1* | 3/2005 | Lefevre .................. A61B 19/52 600/595 |
| 2005/0143831 | A1 | 6/2005 | Justin et al. |
| 2005/0143832 | A1 | 6/2005 | Carson |
| 2005/0171612 | A1 | 8/2005 | Rolston |
| 2007/0100462 | A1 | 5/2007 | Lang et al. |
| 2007/0233269 | A1* | 10/2007 | Steines .................. A61B 5/107 623/20.21 |
| 2008/0133020 | A1 | 6/2008 | Blackwell et al. |
| 2008/0144393 | A1 | 6/2008 | Lee et al. |
| 2009/0276045 | A1* | 11/2009 | Lang .................. A61F 2/30756 623/14.12 |
| 2009/0299481 | A9 | 12/2009 | Romagnoli |
| 2011/0029093 | A1* | 2/2011 | Bojarski ............. A61F 2/30942 623/20.35 |
| 2013/0166037 | A1 | 6/2013 | Goodfellow et al. |

FOREIGN PATENT DOCUMENTS

| | | |
|---|---|---|
| JP | 2009513187 A | 4/2009 |
| NZ | 252360 A | 3/1997 |
| WO | WO 2003/061522 A2 | 7/2003 |
| WO | WO-03061522 A2 | 7/2003 |
| WO | WO-2006118822 A2 | 11/2006 |
| WO | WO 2007041375 A2 | 4/2007 |
| WO | WO 2008/144393 A1 | 11/2008 |
| WO | WO 2010/042941 A2 | 4/2010 |
| WO | WO 2010/045537 A1 | 4/2010 |
| WO | WO-2011028624 A1 | 3/2011 |

OTHER PUBLICATIONS

Notification of Transmittal of the International Search Report and the Written Opinion of the International Searching Authority dated Oct. 12, 2011 in connection with International Patent Application No. PCT/GB2011/050486.

Notice of Reasons for Rejection dated Dec. 9, 2014 in connection with Japanese Patent Application No. 2012-556591; 10 pages.
Further Examination Report dated Dec. 15, 2014 in connection with New Zealand Patent Application No. 627495; 3 pages.
"Australian Application No. 2011225836, Examination Report mailed Aug. 19, 2015", 7 pgs.
"New Zealand Application No. 627495, Examination Report mailed Sep. 4, 2015", 2 pgs.
"U.S. Appl. No. 13/583,902, Non Final Office Action mailed Mar. 21, 2014", 12 pgs.
"U.S. Appl. No. 13/583,902, Notice of Allowance mailed Aug. 7, 2014", 7 pgs.
"U.S. Appl. No. 13/583,902, Preliminary Amendment filed Sep. 10, 2012", 11 pgs.
"U.S. Appl. No. 13/583,902, Response filed Jul. 21, 2014 to Non Final Office Action mailed Mar. 21, 2014", 18 pgs.
"Australian Application No. 2011225836, Response filed Oct. 15, 2015 to Examination Report mailed Aug. 19, 2015", 44 pgs.
"Australian Application Serial No. 2011225836, First Examination Report mailed Mar. 5, 2014", 4 pgs.
"Australian Application Serial No. 2011225836, Response filed Jul. 22, 2015 to First Examination Report mailed Mar. 5, 2014", 15 pgs.
"Chinese Application Serial No. 201180012813.7, Office Action mailed Apr. 3, 2015", (W/ English Translation), 12 pgs.
"Chinese Application Serial No. 201180012813.7, Office Action mailed Dec. 18, 2015", (W/ English Translation), 8 pgs.
"Chinese Application Serial No. 201180012813.7, Response filed Feb. 22, 2016 to Office Action mailed Dec. 18, 2015", (W/ English translation of claims), 7 pgs.
"Chinese Application Serial No. 201180012813.7, Response filed Sep. 10, 2015 to Office Action mailed Apr. 3, 2015", (W/ English translation of claims), 23 pgs.
"European Application Serial No. 11714813.0, Communication Pursuant to Article 94(3) EPC mailed Mar. 1, 2016", 4 pgs.
"European Application Serial No. 11714813.0, Communication pursuant to Rules 161(1) and 162 EPC mailed Oct. 23, 2012", 2 pgs.
"European Application Serial No. 11714813.0, Response filed Apr. 17, 2013 to Communication pursuant to Rules 161(1) and 162 EPC mailed Oct. 23, 2012", 11 pgs.
"International Application Serial No. PCT/GB2011/050486, International Preliminary Report on Patentability mailed Sep. 20, 2012", 12 pgs.
"International Application Serial No. PCT/GB2011/050486, International Search Report mailed Oct. 12, 2011", 8 pgs.
"International Application Serial No. PCT/GB2011/050486, Written Opinion mailed Oct. 12, 2011", 10 pgs.
"Israel Application Serial No. 221653, Examination Report mailed Mar. 2, 2015" (W/ English translation of claims), 2 pgs.
"Japanese Application Serial No. 2012-556591, Office Action mailed Nov. 10, 2015", (W/ English Translation), 4 pgs.
"Japanese Application Serial No. 2012-556591, Response filed Feb. 9, 2016 to Office Action mailed Nov. 10, 2015", (English Translation of Claims), 7 pgs.
"New Zealand Application Serial No. 627495, Office Action mailed Sep. 4, 2015", 2 pgs.

* cited by examiner

TIBIAL PROSTHETIC COMPONENT FOR A PARTIAL OR UNICONDYLAR BEARING KNEE REPLACEMENT, METHOD OF SELECTING SUCH A TIBIAL PROSTHETIC COMPONENT, METHOD OF IMPLANTING SUCH A TIBIAL PROSTHETIC COMPONENT AND A KIT FOR A SURGEON

CROSS-REFERENCE TO RELATED APPLICATION(S)

The present application is a continuation of U.S. patent application Ser. No. 13/583,902 filed Feb. 6, 2013, which claims priority under 35 U.S.C. §365 to International Patent Application No. PCT/GB2011/050486 filed Mar. 11, 2011. International Patent Application No. PCT/GB2011/050486 claims priority under 35 U.S.C. §365 and/or 35 U.S.C. §119(a) to United Kingdom Patent Application No. 1004068.1 filed Mar. 11, 2010. All of these prior applications are incorporated herein by reference into the present disclosure as if fully set forth herein.

FIELD OF THE INVENTION

This invention concerns a tibial prosthetic component for a partial or unicondylar bearing knee replacement, and in particular a partial or unicondylar meniscal bearing knee replacement, a method of selecting such a tibial prosthetic component, a method of implanting such a tibial prosthetic component during knee surgery, and a kit for surgeons.

The knee comprises three inter-dependent joints in three separate compartments, all surrounded by a fibrous capsule covered by the skin. The medial tibio-femoral joint involves contact between the thigh bone (the femur) and the leg bone (the tibia) on the inside of the lower limb. The lateral tibio-femoral joint involves contact between the femur and the tibia on the outside of the lower limb. The patello-femoral joint involves contact between the femur and the knee cap (the patella) on the front of the lower limb.

The front of the lower (distal) end of the femur comprises a flanged concave groove providing a track for the patella. The back of the distal femur divides into two separate near-spherical convex condyles making contact with the tibia. The upper surface of the tibia is like a plateau which is slightly dished on the medial side for contact with the medial femoral condyle forming the medial tibio-femoral joint and slightly convex on the lateral side for contact with the lateral femoral condyle forming the lateral tibio-femoral joint with a protrusion (the tibial eminence) running from front to back between the joints.

The articulating surfaces in each joint are covered with thin layers of a tough protective layer, called cartilage, and are lubricated by synovial fluid secreted from a membrane on the inner surface of the fibrous capsule surrounding the knee. The surfaces of the tibio-femoral joints are further separated by the menisci, semi-circular semi-lunar collagen bundles oriented circumferentially. Each bundle is securely attached at each end to the tibia and loosely to the peripheral capsule. The menisci form closely fitting mobile sockets for the femoral condyles bringing the dissimilar surfaces of the femur and tibia into closer conformity while allowing some antero-posterior translation of the femoral condyles on the tibia.

The bones are held together actively by muscles with their tendons which span the joints and passively by ligaments and the joint capsule. The ligaments comprise bundles of collagen fibres running mainly longitudinally. The collateral ligaments arise on the external surfaces of the medial and lateral condyles. The medial collateral ligament inserts into the external medial surface of the proximal tibia. The lateral collateral ligament inserts into the proximal surface of the fibula. The medial collateral ligament is a much larger and stiffer structure than the lateral collateral ligament. The cruciate ligaments arise from the internal surfaces of the femoral condyles and insert into the tibial eminence.

The ligaments and the bones together form a mechanism which controls a complex pattern of movement of the bones on each other. In the unloaded state, flexion of the knee to 130° about a transverse axis is accompanied by approximately 25° rotation about the axis of the tibia (axial rotation) and approximately 5° about an antero-posterior axis (abduction-adduction). These movements are accommodated by mainly antero-posterior translations of the tibio-femoral contact areas so that the bones roll as well as slide on each other. Additionally, the femoral condyles can move angularly about the axis of the tibia. Under load, the ligaments stretch and the articular surfaces indent, significantly modifying the relationship between flexion, axial rotation and abduction-adduction and between flexion and contact area translations. Movements at the knee are therefore load and activity-dependent. Damage to the articular surfaces or to the ligaments changes the patterns of movement of the bones on each other and response of the joint to load.

Osteoarthritis follows from failure of the cartilage in one or other of the three joints, leading to bone-on-bone contact and the onset of pain. Frequently, osteoarthritis first manifests itself in the medial compartment, while the ligaments remain intact. The disease can remain confined to the medial compartment until the anterior cruciate ligament fails and the disease then spreads to the other two compartments. No drug-based treatment has been found which halts or reverses these processes.

Total knee replacement is the most common surgical treatment for osteoarthritis, involving replacement of the articular surfaces of all three compartments and sacrifice of some of the ligaments. Partial knee replacement involves replacement of the articular surfaces in only one compartment, leaving intact the surfaces of the other two compartments and all of the ligaments. Partial knee replacement can act prophylactically, reducing the rate of development of the disease in the other compartments. Partial knee replacement is surgically more demanding and is not always used when it is indicated.

To implant the prosthetic components of a knee replacement, sufficient sections of bone have to be removed from the surfaces of the tibia and the femur.

It has been appreciated that, for a person having a small knee joint, cutting away sections of the tibia to make way for the tibial prosthetic component can weaken the bone surrounding the components to such an extent as to cause bone to break off and can also cause ligaments to detach. In addition, in medial partial knee replacements, removal of too much bone can result in inadvertent damage to the medial collateral ligament, which can result in overstuffing the replaced compartment and overloading the intact lateral compartment, leading to its eventual degeneration.

Currently there are a range of sizes of tibial implants provided for use with a range of sizes in patients. In one embodiment of the Oxford Knee there are medial plates with sizes AA to F. They have a central plate whose peripheral thickness is 2.95 mm, a keel whose depth is 9 mm and whose thickness is 2.75 mm. All of the differently sized tibial implants have the same thickness plate and depth and thickness of keel. A size A tibial implant has a length of 45.4 mm, a size B a length of 48.6 mm, a size C a length of 51.8 mm, a size D a length of 55 mm, and a size F a length of 58.2 mm. The keel lengths of the implants from A to F, are 28 mm, 30 mm, 33 mm, 35 mm, 38 mm, and 40 mm.

REALISATION OF THE INVENTION

We have come to realise that having plates of the same depth for large people and small people is wrong. It causes more bone to be cut off the tibia than is necessarily desirable for small people. Also, having keels of the same depth and width can be a problem for small people, and may result in an unnecessarily weakened tibia.

Currently, large and extra large people do not have significant problems with their tibial implants being too weak. Paradoxically, because they have a smaller length, but the same thickness plate and width of keel, smaller tibial implants are even stiffer than larger ones, even though they will have to accommodate less stress in use. We think that current tibial implants for smaller people are over-engineered and can be made with thinner plates and/or shallower keels, and/or thinner keels.

In general, we believe that tibial implants for smaller people can be made to withstand the same stresses as larger implants, or even perhaps parametrically less strong (e.g. linearly in line with height, weight, BMI, etc).

SUMMARY OF THE INVENTION

According to a first aspect of the invention there is provided a tibial prosthetic component comprising a plate for forming a tibial plateau of a tibia, wherein a peripheral region of the plate has a thickness of less than 3 mm, preferably less than 2.5 mm, and optionally 2.25 or 2.0 mm±0.5 mm or ±0.2 mm, or ±0.1 mm.

In some embodiments the peripheral region of the plate may have a thickness of less than 2.0 mm, and may have a thickness of less than 1.8 mm, or less than 1.7 mm. In some embodiments the peripheral region of the plate may have a thickness of between 1.9 mm or 1.8 mm and 1.5 mm.

In some embodiments we can determine the appropriate thickness of a tibial component from the body height of a patient. This works on the following constraints:

The body mass index (BMI) of a patient does not exceed a set value (around 30-35).

$$BMI = body\ mass\ (kg)/(body\ height\ (m))^2$$

The same material is used for all sizes of component, giving a constant maximum allowable stress.

The length of the component, the width of the component and the height of the patient are all proportional to one another for a given maximum BMI.

Using these constraints, it has been found that the component thickness is proportional to the height of the patient.

Using finite element stress analysis, and varying the anterior-posterior length of the keel between acceptable limits, it has been found that the tibial plate can be reduced by a factor of 0.25 of a maximum thickness.

Using the original plate thickness of 3 mm as the maximum, this equates to a "minimum" thickness of 2.25 mm. We may go thinner than that, for example, where the 'maximum' plate thickness is smaller than 3 mm.

Because of the proportionality constraint, this ratio is also used to determine a suitable range of patient heights. For example, for a maximum height of 6'4", the minimum height will be 4'10". This range can be adjusted according to patient records.

As the thickness of the peripheral region of the plate is less than the current 3 mm thickness of conventional plates, a thinner region of the tibial bone has to be cut away to accommodate the peripheral region of the plate, thereby reducing the chances of the bone being unduly weakened and damage being caused to the ligaments attached to the tibia. It has been realised that the thickness of the plate can be reduced because, at least for smaller persons, the plate does not have to be 3 mm thick to withstand the forces normally present in the knee. These advantages generally increase as the plate is made thinner until the plate becomes too thin to withstand the forces present in use. Accordingly, the thickness of the peripheral region of the plate is ideally greater than or equal to that which is required to withstand the forces normally present in the replaced compartment. It is believed that a thickness of less than 2.5 mm and preferably between 1 and 2.5 mm meets these requirements, for example between 1 and 1.9 mm, such as between 1.5 and 1.8 mm.

The tibial prosthetic component may comprise a keel projecting from the plate, the keel arranged to extend into the tibia, in use. The keel may comprise an elongated projection having a length in an anterior to posterior direction longer than a width in a lateral to medial direction. The keel acts as an anchor for securing the plate in place on the tibia. Such keels are known in the Oxford Knee and other knee tibial components.

The keel projection may extend downwardly, in use, from a region in an innermost half of the plate. In this way, the distance between the keel and an outer surface of the tibia is increased, reducing the chance that implantation of the prosthetic component weakens the bone and causes the bone to break away.

A major surface of the projection may be arranged to be at an angle to the perpendicular to the plate so as to extend generally parallel with or away from an outer surface of the tibia, when implanted. The major surface of the projection may curve parallel with or away from a curved outer surface of the tibia, in use. The projection may extend in a plane and may be arranged such that the plane is at an angle to the vertical, in use/a normal to a plane of the plate. The projection may be arranged such that, in use, the distance between an outer surface of a condyle of the tibia and the major surface and ends of the projection is roughly constant or increases as one moves downwardly along the extent of the projection.

An end of the projection located posteriorly and/or anteriorly, in use, may extend at an angle of less than 90 degrees to a longitudinal direction of the projection. In one embodiment, the end of the projection located posteriorly, in use, is curved, with the radius of curvature being at least 2.0, and possibly approximately 2.5 or 3.0 mm or more. The radius of curvature of the end may be about half the keel depth, which may be between 3.5 mm and 4.5 mm (inclusive). We have found that a higher radius of curvature for the ends of the keel (higher than the current 1.5) gives greater capacity to handle stress, and possibly allows the keel to be made shallower and/or shorter in the anterior-posterior direction. This may be a separate invention. By having a shallower and/or shorter keel we reduce the amount of bone that needs to be removed at the posterior of the tibia, (or anterior) reducing weakening of the bone in this area compared to previous known Oxford tibial prosthetic components having keels.

The keel may comprise webs extending from the projection to brace the projection against the plate. The webs strengthen the connection of the plate to the projection and/or make the projection more rigid than it would be without the webs, reducing the chance of the projection breaking away or being bent, in use. The webs may also stiffen/reinforce the plate compared to how it would be without the webs, allowing thinner plates to be used. The webs may comprise a continuous brace such that there are no gaps between each web and the projection and the plate. Alternatively, the webs may comprise struts or a continuous brace having holes therein such that there are gaps in or between each web and the projection and/or plate. By providing gaps, over time bone may grow into the gaps further securing the prosthetic component in place. In addition specialist porous coatings which may or may not include Hydroxyapaptite may be added that encourage bony ingrowth.

The keel projection may comprise a slot therein, possibly for receiving cement or bone growth.

As mentioned above, the thickness of the plate may be proportional to the height of a patient (or other characteristic, such as weight). Other dimensions of the plate may be arranged to be proportional to the plate thickness (and so to the patient characteristic). For example, the length of the plate may be proportional to the thickness of the plate. Thus a suitable plate may be selected for a patient based on its length rather than its thickness (as thickness is proportional to length).

Alternatively, or additionally, the breadth of the plate (in its longest dimension, i.e. at the plate's widest part) may be proportional to the thickness and/or length of the plate.

Alternatively, or additionally, the depth and/or length of the keel (if present) may be proportional to the length and/or thickness and/or breadth of the plate. Thus the dimensions of a plate may scale in proportion to the height of a patient.

The ratio of plate length to plate thickness (length/thickness) may be approximately 20.25±5, or ±2, or ±1, or ±0.5, or ±0.3, or ±0.2 or ±0.1. The ratio of plate length to keel depth (length/keel depth) may be 6.75±2, or ±1, or ±0.5, or ±0.3, or ±0.2 or ±0.1.

The thickness and/or keel depth and/or length of the plate may be arranged to be proportional to a physical attribute of a patient other than (or additional to) height, such as the weight of the individual, size of lateral or medial condyle of the tibia, length of the tibia, length of the femur, and a gap between the tibia and the femur.

The peripheral region of the plate that has a thickness of less than 3 mm may be a peripheral region having an edge that is arranged to be located in substantial alignment with an edge of the tibia. For example, for a lateral tibial prosthetic component, a peripheral region of the plate may have an edge arranged to be located, in use, in substantial alignment with the lateral, anterior and posterior sides of the tibia and, for a medial tibial prosthetic component, a peripheral region of the plate may have an edge arranged to be located, in use, in substantial alignment with the medial, anterior and posterior sides of the tibia. An innermost peripheral region of the plate to be located, in use, adjacent to the intercondylar eminence of the tibia and/or a central region of the plate may have a thickness of 3 mm or more.

A flange may extend, in use, upwardly from the innermost peripheral region (possibly at a normal to a plane of the plate). The flange may provide an abutment surface for locating a meniscal bearing of a prosthetic knee joint.

It may be possible to cut a deeper recess in areas of the tibia away from an outer edge of tibia without weakening the bone unacceptably and therefore, it may only be necessary that peripheral regions of the plate that, in use, lie close to an outer edge of the tibia are of reduced thickness. However, in a preferred embodiment, all of, or the majority of the area of the plate has a thickness of less than 3 mm, for example the plate may have a thickness of less than 3 mm other than in regions made thicker by the presence of the keel and/or flange. By "majority of the area of the plate" we may mean more than 50%, or ≥70%, or ≥80%, or even ≥90%.

A thickness of a central region of the plate may be less than the thickness of the periphery of the plate, for example to provide a pocket on the lower surface for receipt of cement or porous material for cementless implantation.

The thickness of the plate may vary. An upper surface of the plate may be convex or concave and a lower surface of the plate may be substantially flat. However, in an alternative embodiment, the lower surface of the plate be shaped such that regions of the plate other than the peripheral region extend into the tibia, in use, more than the peripheral region of the plate. For example, the lower surface could be convex or stepped with the plate increasing in thickness, possibly to a thickness of 3 mm or more, as one moves inwardly from the peripheral region of the plate.

According to a second aspect of the invention, there is provided a method of selecting a tibial prosthetic component comprising using measurements of at least one physical attribute of an individual into whom the tibial prosthetic component is to be implanted to select a tibial prosthetic component from a range of components whose thickness of plate and/or depth of keel differs.

In practice at present a surgeon cuts away a sliver of the tibia up to 3 mm thick to accommodate the tibial implant and uses the removed sliver to size the appropriate size of tibial implant by holding the sliver of bone against trial templates (of the opposite knee).

Using our new realisation, a tibial prosthetic component may be provided that is appropriate for the individual into whom the tibial prosthetic component is to be implanted. The physical attribute may be one or more of a height of the individual, weight of the individual, size of lateral or medial condyle of the tibia, length of the tibia, length of the femur, and a gap between the tibia and the femur. Imaging techniques, e.g. X-rays or MRI could be used to image a person's tibia and the images could provide the size indicator. For example, the size of the tibial condyle to be selected can be estimated from an image of it, and a preliminary view of the size of tibial component needed could be taken. A depth of tibia consistent with the thickness of tibial plate of that sized tibial component would be removed.

According to another aspect the invention comprises a kit of a plurality of different sizes of tibial prosthetic component (or trial component) for a partial or unicondylar meniscal knee prosthetic, each of the tibial components having a plate adapted in use to contact against a meniscal bearing and wherein at least a larger one of the tibial implants has a thicker plate than at least a smaller one of the tibial implants.

Each tibial component in the kit may be for use with an individual having a particular height, or an individual having a height within a predetermined range of heights.

The tibial component may have a keel.

The kit may have several sizes of implants and different sized implant may have a different plate thickness. However, it may be preferable to have fewer different plate thicknesses than there are implants sizes, possibly only 2 or 3 different plate thicknesses. For example, there may be size A to F of implant sizes and A to B or C or D may have the same, smaller, thickness of plate, and sizes C or D or E to F may have a larger thickness of plate.

The thicker plate may be 3.0 mm thick (±0.3 mm, or 0.2 mm, or 0.1 mm) and the thinner plate may be 2.0 mm thick, or 2.25 mm thick, (±0.5 mm, or 0.4 mm, or 0.3 mm, or 0.2 mm, or 0.1 mm).

Interestingly, the ratio of the length of the A size tibial insert to the F size tibial insert is about ¾. We believe that the thickness of the plate can be reduced linearly in proportion. Since grade F plates are 3.0 mm thick (they are all 3.0 mm thick up until now) we believe that ¾ (3.0) mm=2.25 mm thick plate will be strong enough for a grade A prosthetic.

The ratio of plate length to plate thickness (length/thickness) may be approximately 20.25±0.5, or 0.3, or ±0.2 or ±0.1, where the thickness of the plate may be less than 3 mm. For example, a grade A prosthetic may have a thickness of 2.25 mm, a grade B prosthetic may have a thickness of 2.4 mm, a grade C prosthetic may have a thickness of 2.55 mm, a grade D prosthetic may have a thickness of 2.7 mm and a grade E prosthetic may have a thickness of 2.85 mm.

Other proportionality relationships between plate length and thickness may be possible. However, it is preferred that each grade of plate has a plate thickness which is substantially the same proportion of that plate's length (e.g. 5%), such that within the kit plate thickness is proportional to plate length. Plate thickness and plate length may also be proportional to a patient characteristic, such as patient height or BMI.

We believe that for smaller grades of tibial implant we can have smaller (e.g. shallower) keels, either with or without thinner plates.

Again, the prior art has had the keel depth fixed for all size tibial implants. We believe that the keel depth should be smaller for smaller implants. Also, in addition or alternatively, the thickness of the keel and/or its length should be smaller for smaller implants.

The ratio of plate length to keel depth (length/keel depth) may be 6.75±0.5, or ±0.3, or ±0.2 or ±0.1, where the depth of the keel may be less than 9 mm. For example, a grade A prosthetic may have a keel depth of 6.75 mm, a grade B prosthetic may have a keel depth of 7.2 mm, a grade C prosthetic may have a keel depth of 7.7 mm, a grade D prosthetic may have a keel depth of 8.15 mm and a grade E prosthetic may have a keel depth of 8.6 mm.

Other relationships between plate length and keel depth may be possible. However, it is preferred that each grade of plate has a keel depth which is substantially the same proportion of that plate's length (e.g. 15%), such that in the kit keel depth is proportional to plate length. Keel depth and plate length may also be proportional to a patient characteristic, such as patient height or BMI.

Alternatively, there maybe fewer different keel depths than there are different sizes of tibial component, possibly only 2 or 3 different depths. For example tibial components of size A, B, and possibly C and/or D could have a "small" keel depth and sizes F, E, and possibly D and/or C could have a "large" keel depth (i.e. C and D sizes could in some versions both be large, or small, or C could be small and D could be large).

The depth of the keel may also be proportional to the thickness of the plate, and may also be proportional to the length of the keel and/or the breadth of the plate.

According to another aspect the invention comprises a set of differently sized tibial implant components (or trial implant components) for a meniscal partial or unicondylar prosthetic knee having a tibial component, a femoral component, and a meniscal bearing, the tibial component having a bearing surface against which in use the meniscal bearing bears, and a keel that extends away from the bearing surface and into the tibia, in use, and wherein the keel depth of a larger sized tibial component is deeper than the keel depth of a smaller sized tibial component.

Each tibial component in the kit may be for use with an individual having a particular height, or an individual having a height within a predetermined range of heights.

There maybe fewer different keel depths than there are different sizes of tibial component, possibly only 2 or 3 different depths. For example tibial components of size A, B, and possibly C and/or D could have a "small" keel depth and sizes F, E, and possibly D and/or C could have a "large" keel depth (i.e. C and D sizes could in some versions both be large, or small, or C could be small and D could be large).

A suitable keel depth for a size A component or trial component would be 6.75 mm.

We believe that the keel depth of the tibial component has an important role in fractures at the top of tibia with partial or unicondylar meniscal prosthetic knees, especially in patients of smaller stature. For example many oriental people (e.g. women) are "small" or "extra small" by Western European sizings of tibial implants. We believe that keel depth (and possibly keel length) can safely be reduced linearly in proportion to the length of the tibial component plate, which in turn is generally linearly related to the height of a patient. Thus a patient who is 75% of the height of a very tall person (6 ft 4") could, we believe, enjoy a keel depth that is only 75% of the maximum currently used (all keel depths for the Oxford Knee are currently 9 mm).

Varying keel depth parametrically with a physical parameter of a patient (e.g. height) may help reduce problems in smaller patients. The depth of the keel may be arranged to be proportional to the parameter of the patient. The depth of the keel may also be proportional to the length of the plate, and may also be proportional to the thickness of the plate and/or the length of the keel and/or the breadth of the plate. The ratio of plate length to keel depth (length/keel depth) may be 6.75±2, or ±1, or ±0.5, or ±0.3, or ±0.2 or ±0.1.

The keel abuts the tibial plate and their join has a radiussed connection point. We have also come to understand that the radius of curvature of the connection point can influence the strength of the component, and hence how thin the plate can be made, and how shallow the keel can be. In the prior art the radius of curvature is 1.5 mm. We believe that better results are possible if it is 3.0 mm or more.

It will be appreciated that a surgeon will take into the operating theatre a set of templates for the tibial component—"dummy" or "trial" pieces that are used to select the correct size of tibial component and that are test-fitted to the tibia. Definitions of invention referring to "tibial component" apply just as well to trial tibial components/templates, and to sets of trial or template tibial components. Protection for trial components and sets or kits of trial components is intended.

In order to remove 2.25 mm (or some other depth that is less than 3.00 mm) of bone from the tibia (instead of the prior art 3.00 mm) the surgeon will have to have a differently set up sawing jig, set to that depth. Such a jig may be a component in a tool set provided as a kit. There may be more than one sawing jig, of different depth, provided.

If a shallower keel is used (or a thinner one) a different cutting saw may be needed to cut to the new depth. Such a different saw may form part of a kit of tools provided to the surgeon. There may be more than one keel saw provided, each of different depth.

It will be appreciated that a feature of a tibial component described in relation to one of the aspects of the invention discussed above may, where appropriate, also be employed in any of the other aspects of the invention.

BRIEF DESCRIPTION OF DRAWINGS

Embodiments of the invention will now be described, by example only, with reference to the accompanying drawings, in which.

DESCRIPTION OF EMBODIMENTS

Figure 1A:
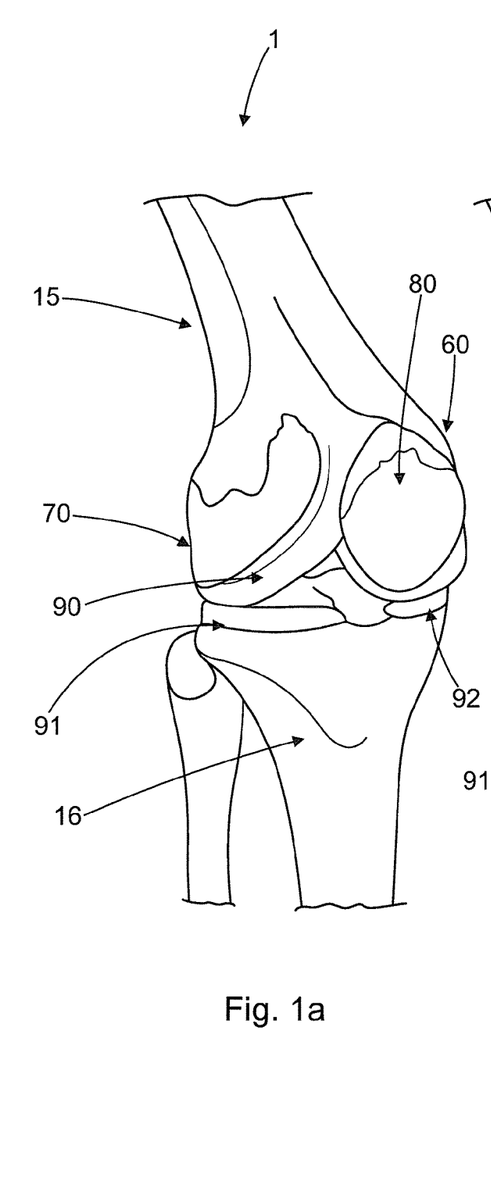
FIG. 1a is a perspective view of bones of a knee joint.
Figure 1B:
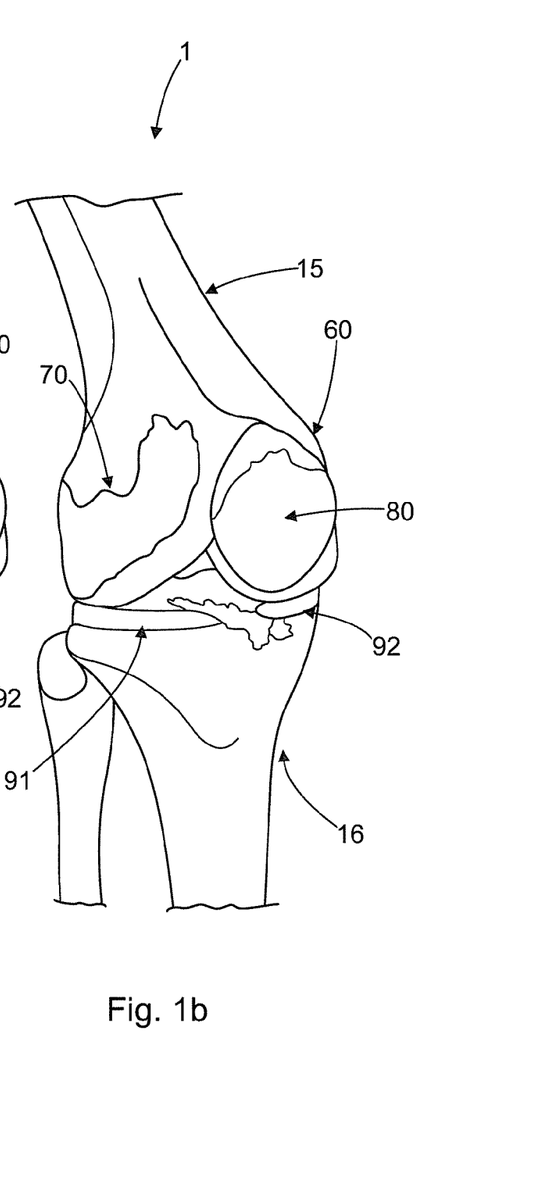
FIG. 1b is a perspective view of bones of a knee joint of an individual suffering from arthritis.

FIG. 1a shows a healthy knee joint 1 and FIG. 1b shows a knee joint showing progressive knee joint degeneration. The knee joint 1 is where the end of the femur 15 meets the top of the tibia 16. The end of the femur 15 consists of two condyles 60, 70. These condyles 60, 70 sit on top of the tibia 16, which is like a platform. Thus, on each side of the joint 1, there is an area of contact between the two bones. When the knee is bent, the condyles 60, 70 of the femur 15 roll and slide on top of the tibia 16 at these two areas of contact. A third bone, the kneecap (patella) 80, glides over the front and end of the femur 15.

In a healthy knee joint (FIG. 1a), the surfaces of these bones are very smooth and covered with cartilage—a tough protective tissue. The articular disks of the knee-joint are called menisci 91, 92 because they only partly divide the joint space. These two disks, the medial meniscus 91 and the lateral meniscus 92, consist of connective tissue with extensive circumferential collagen fibres containing cartilage-like cells. Strong fibres run along the menisci 91, 92 from one attachment to the other, while weaker radial fibres are interlaced with the former. The menisci 91, 92 are flattened at the centre of the knee joint, fused with the synovial membrane laterally, and can move over the tibial surface 16. Also in a healthy knee joint is the articular cartilage 90, also called hyaline cartilage which is the smooth, glistening white tissue that covers the surfaces of all the diarthrodial joints in the human body.

The menisci 91, 92 help transmit the compressive force from tibia to femur, and serve to protect the ends of the bones from rubbing on each other and to effectively deepen the tibial sockets into which the femur 15 attaches. They also play a role in shock absorption, and may be cracked, or torn, when the knee is forcefully rotated and/or bent. FIG. 1b shows a knee joint 1 in which arthritis has caused damage to one or more of the bone surfaces and cartilage where the bones rub together. In particular, osteoarthritis is a condition where the surface of the joint is damaged, resulting in bone against bone contact. The contact can cause severe pain and eventually loss of movement. In some cases, there may be significant damage on only one side of the joint so only one of the condyles may be damaged. In these cases, a partial (unicompartmental) knee replacement may be considered. In a partial knee replacement, only one side of the joint 1 is resurfaced.

Figure 1C:
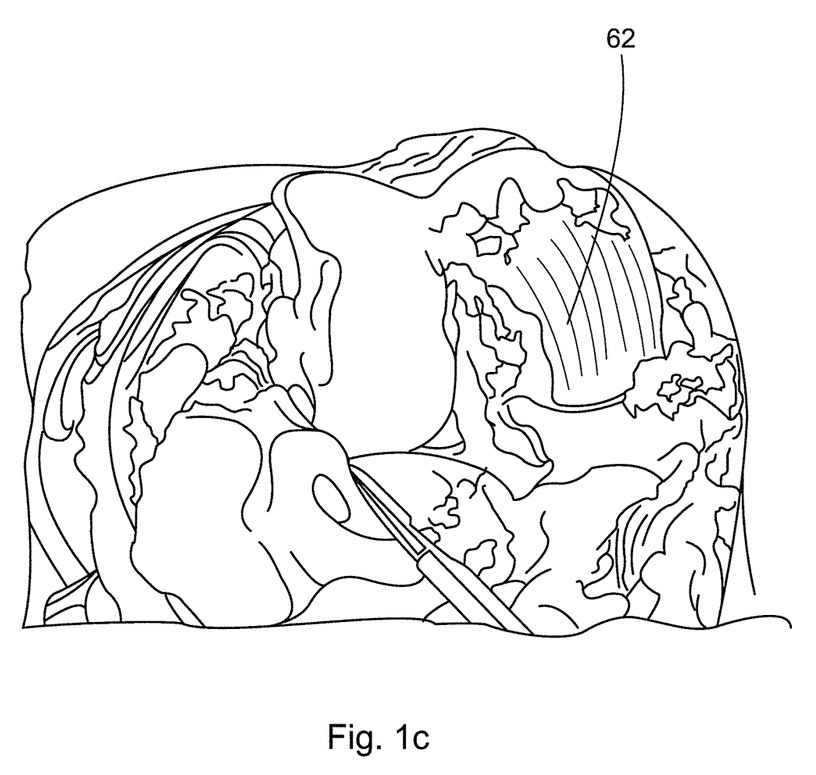
FIG. 1c is a photograph showing the effects of antero-medial osteoarthritis on a knee.

The effects of arthritis, and in particular antero-medial osteoarthritis, can more clearly be seen in FIG. 1c. FIG. 1c shows at 62 wear on the medial femoral condyle which has been caused by direct contact between the femoral condyle and the exposed bone on the tibial plateau.

Figure 2:
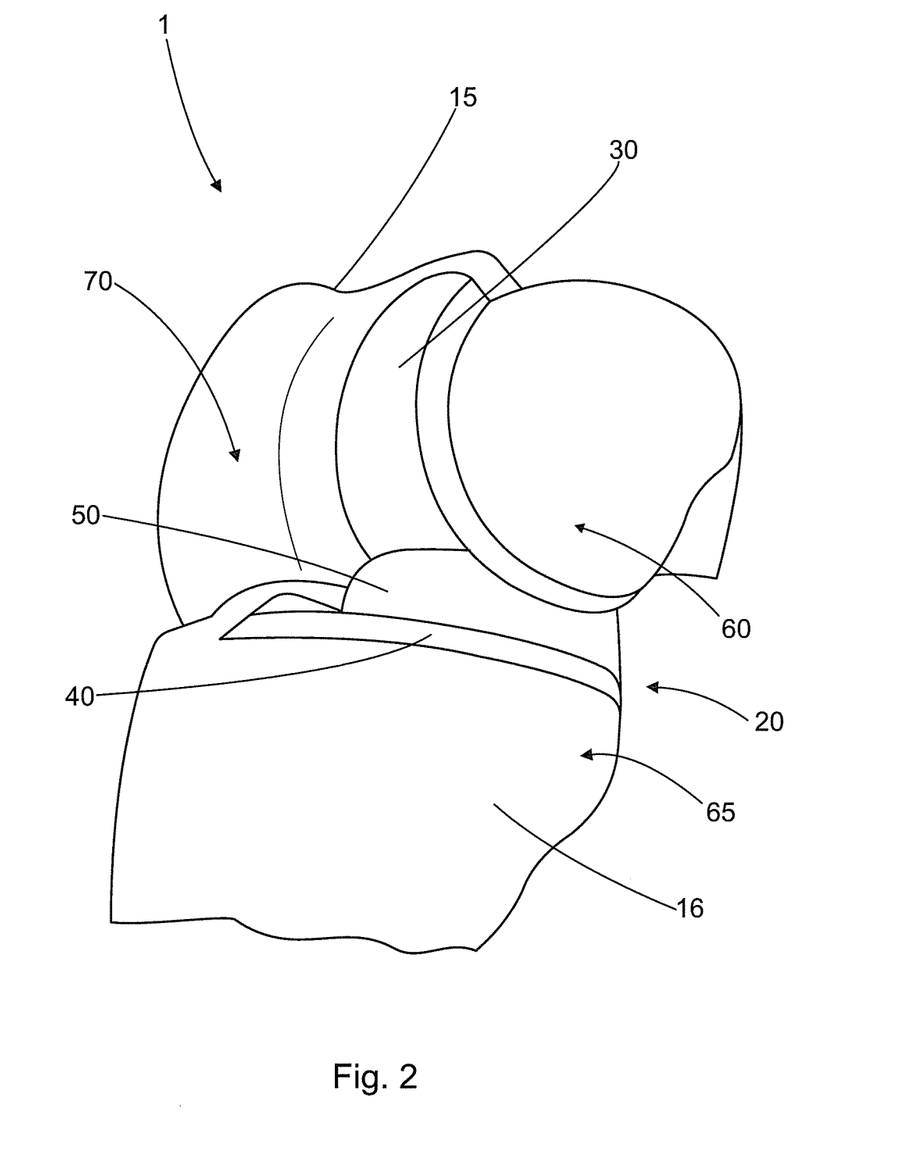
FIG. 2 is a perspective view of a knee joint into which a prosthetic partial knee replacement according to an embodiment of the invention has been implanted.

Referring to FIG. 2, a partial knee replacement is shown comprising a tibial prosthetic component 40, a mobile meniscal bearing 50 and a femoral prosthetic component 30. The tibial prosthetic component 40 and femoral prosthetic component 30 are implanted in recesses cut into a tibial condyle 65 and a femoral condyle 60 respectively and fixed to the bones with cement or post-operative bone growth.

Figure 3:
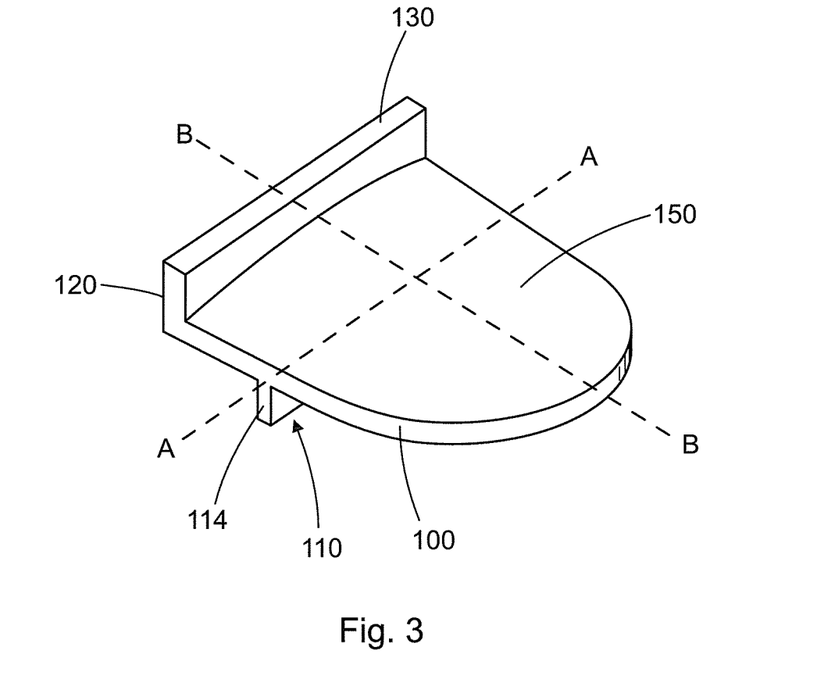
FIG. 3 is a perspective view of a tibial prosthetic component according to one embodiment of the invention viewed from above.

Referring now to FIGS. 3 to 8, the tibial prosthetic component 40 comprises a D-shaped metal plate 100 for replacing a damaged tibial plateau of the tibia 15. In this embodiment, the thickness, x (see FIG. 5), of the majority of the plate is less than 3 mm. However, it will be understood that in other embodiments a peripheral region of the plate (other than that having edge 120) may have a thickness of less than 3 mm with the thickness of the remainder of the plate having a different thickness, for example increasing to above 3 mm as one moves away from this peripheral region, or decreasing further below the thickness of the peripheral region (or the thickness may remain constant). In the example of FIG. 3, x is 2.0 mm+/−0.1 mm or 1.5 mm+/−0.1 mm, or 2.5 mm+/−0.1 mm. In some embodiments, x is between 2.4 mm and 1.7 mm, or between 1.9 mm and 1.5 mm.

The plate 100 extends generally in a plane encompassing lines A-A and B-B.

A keel 110 projects from the plate 100, the keel 110 arranged to extend into the tibia 16, in use. The keel 110 comprises an elongated projection 112 having a length in an anterior to posterior direction longer than its width in a lateral to medial direction. The projection 112 extends longitudinally in a direction generally parallel with an innermost edge 120 of the plate 100. A region of the plate 100 from which the projection 112 extends is located in an innermost half of the plate 100 that is closest to the intercondylar eminence.

Figure 4:
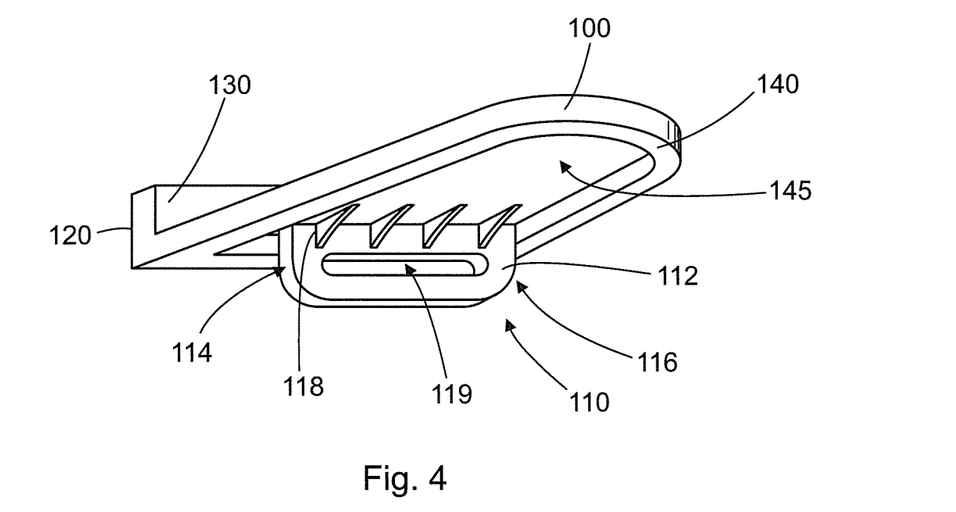
FIG. 4 is a perspective view of a tibial prosthetic component shown in FIG. 3 viewed from below.
Figure 5:
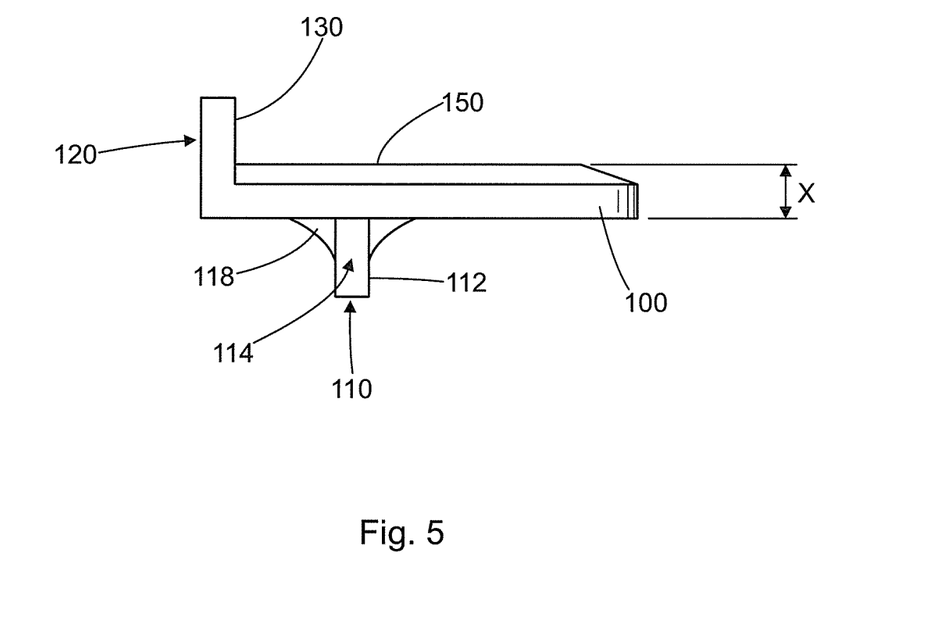
FIG. 5 is a side view of the tibial prosthetic component shown in FIG. 3.

A curved end surface 116 of the keel 110 located posteriorly, in use, extends at a greater angle to the plane of the plate 100 than a curved end surface 114 of the keel 110 located anteriorly, in use. The shape of the curves of the end surfaces 116 and 114 may approximate a posterior and anterior shape, respectively, of an outer posterior and anterior surface, respectively, of the condyle 65 of the tibia 16. In other embodiments the anterior and posterior curved ends of the keel have the same curvature.

Figure 6A:
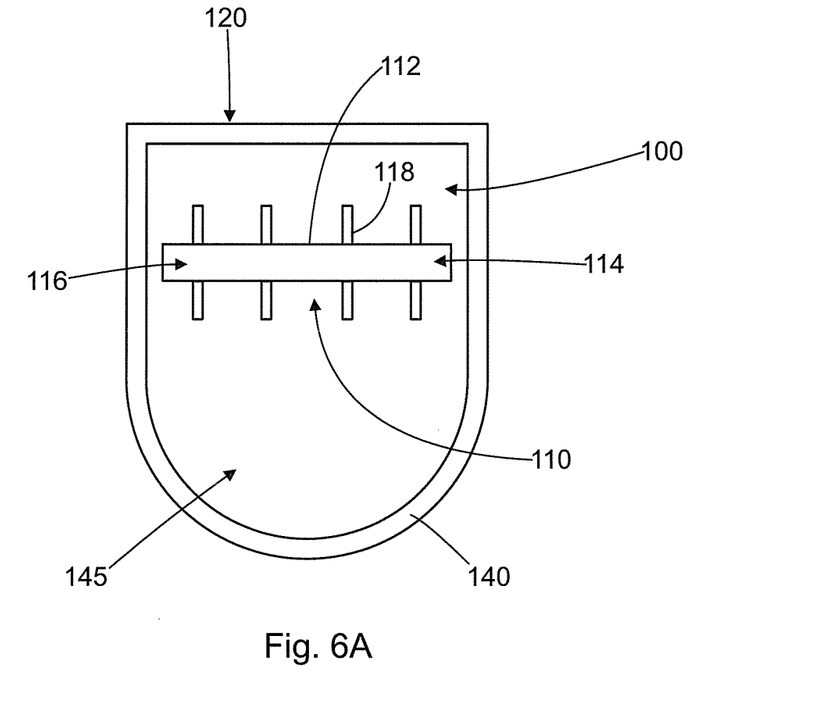
FIG. 6A is a bottom view of the tibial prosthetic component shown in FIG. 3.

The keel 110 further comprises webs 118 extending from either side of the projection 112 to brace the projection 112 against the plate 100 and reinforce the plate 100. In this embodiment, the webs 118 comprise eight substantially triangular sections, having a curved hypotenuse, four located along either side of the projection 112. However, it will be understood that a different number and shape of the webs 118 could be used. The webs 118 strengthen the connection of the plate 100 to the projection 112, reducing the chance of the projection 112 breaking away or being bent, in use, and stiffen the plate 100. The projection 112 further comprises a slot 119 therein for receiving bone cement and/or for bone in-growth.

A flange 130 may extend, in use, upwardly from an innermost peripheral region of the plate 100, in this embodiment, normally to the plane of the plate 100. In use, the flange 130 may locate against the intercondylar eminence 67. The flange 130 may also provide an abutment surface for locating the meniscal bearing 50.

A downwardly extending rim 140 is provided around a periphery, in this embodiment, the entire periphery, of the plate 100 to define a central recess 145. The central region defined by the flange has a thickness which is less that the thickness of the periphery of the plate. The central recess can be used to provide a pocket on the lower surface for receipt of cement or porous material for cementless implantation.

An upper surface 150 of the plate 100 is (in this example) convex both anteriorly-posteriorly and laterally-medially in the case where the tibial component is for a lateral condyle. In the case where the tibial component is for a medial condyle the plate is flat or concave. By increasing the area of the surface 150 over which the bearing 50 moves, wear of the bearing and the tibial prosthetic component is reduced due to the increase in effective contact area between the surface 150 and the bearing 50.

To implant the tibial prosthetic component, a recess is cut into a condyle of the tibia, the recess being, in this example, 2.25 mm deep.

Figure 7:
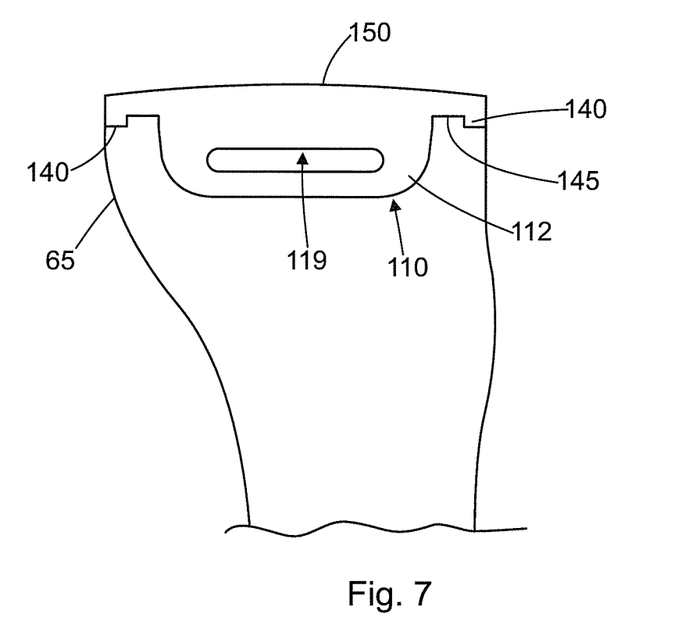
FIG. 7 is a cross-sectional view of the tibial prosthetic component along line A-A of FIG. 3 implanted in a tibia bone.
Figure 8:
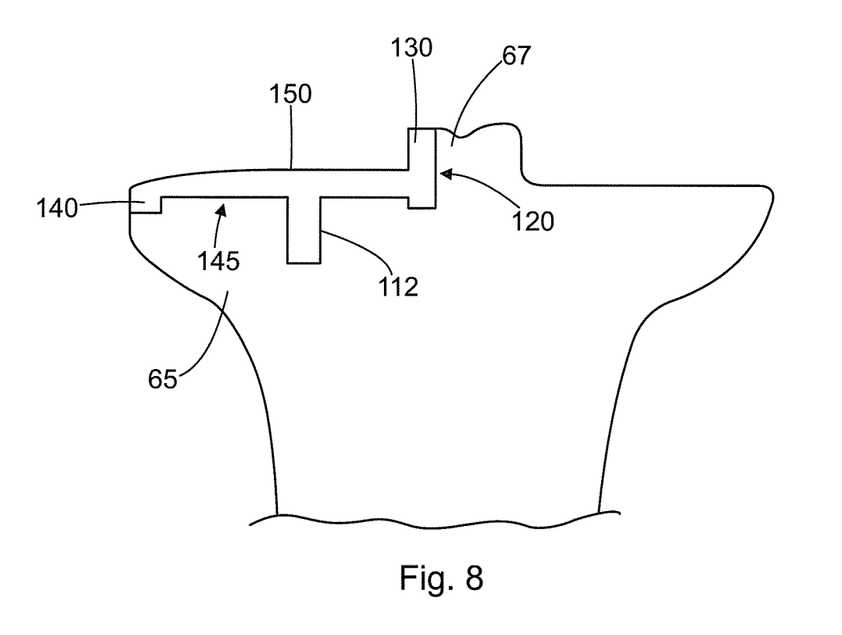
FIG. 8 is a cross-sectional view of the tibial prosthetic component along line B-B of FIG. 3 implanted in a tibia bone.

As the thickness of the plate 100 is less than 3 mm, the depth of the recess does not need to be as great as for conventional tibial prosthetic components having a plate that is 3 mm thick. It has been realised that the thickness of the plate can be reduced because, at least for smaller persons, the plate does not have to be 3 mm thick to withstand the forces normally present in the knee. By reducing the depth of the recess, the likelihood of bone in proximity to the recess breaking away is reduced. This is further aided as the distance between the ends 114, 116 of the keel 110 and the outer surface of the condyle 65 is increased relative to a projection with vertical ends. Accordingly the keel 110 acts as an anchor for securing the plate in place on the tibia, whilst the curved ends 114, 116 reduce the chance of the tibia being overly weakened through implantation of the tibial prosthetic component, and help strengthen the keel/plate connection.

It has been appreciated that having a plate 3 mm thick for all size people is not optimum. A 3 mm thick plate is strong enough for, for example, a 2 m heavily built man and is, we now realise, significantly over-engineered for a 1.5 m, slightly built woman. Removing 3 mm of bone from the tibia condyle of a 2 m heavily built man does not reduce the strength of the bone unacceptably, but removing 3 mm of bone from the tibia condyle of a 1.5 m slightly built woman may weaken the head of the tibia bone unacceptably, and may result in inadvertent damage to the medial or lateral collateral ligament. The prosthetic component of the invention mitigates this problem by providing plates of reduced thickness that can be used on smaller individuals. It has also been appreciated that shallower keels can be used with thinner plates for smaller patients to reduce the risk of bone fracture.

To secure the tibial prosthetic component in place, cement is provided in central recess 145. As well as providing a location for receiving the cement, over time growth of the bone into the central recess 145 may further secure the prosthetic component in place.

Other embodiments are cementless. They typically have the keel slot in the tibia made a bit thinner, requiring the keel to be force-fitted into the slot. Cemented or cementless keels may or may not have a through-hole in their keel. Cementless components may have porous coatings to encourage bony ingrowth.

It may be possible to cut a deeper recess in areas of the tibia away from an outer edge of the tibia without weakening the bone unacceptably and therefore, it may only be necessary that peripheral regions of the plate that, in use, lie close to an outer edge of the tibia are of reduced thickness. Accordingly in an alternative embodiment, a lower surface of the plate is shaped such that regions of the plate other than the peripheral region extend into the tibia, in use, more than the peripheral region of the plate, these regions of the plate possibly having a thickness of 3 mm or more.

A realization of the invention is that different sizes of tibial prosthetic component may be required for different size individuals. Accordingly, according to one embodiment of the invention there is provided a method of selecting a tibial prosthetic component for an individual.

Measurements are taken of at least one physical attribute of an individual into whom the tibial prosthetic component is to be implanted. Alternatively, in practice we believe that the surgeon will, having decided that the patient is slight enough to receive the new thinner plate tibial component, cut away a thinner slice of tibial condyle (e.g. 2.25 mm deep slice). They will then use this removed slice as the physical attribute and hold it against one or more differently sized trial or template tibial components until they are happy that the outlines/areas or overlap are a good match and then select that size of tibial component. They may have made a preliminary assessment that they are likely to use a thinner tibial component, and therefore cut off a thinner slice of tibia in advance of the operation (for example, from looking at images (e.g. X-ray images) of the patient's tibia, or from the height of the patient).

Figure 6B:
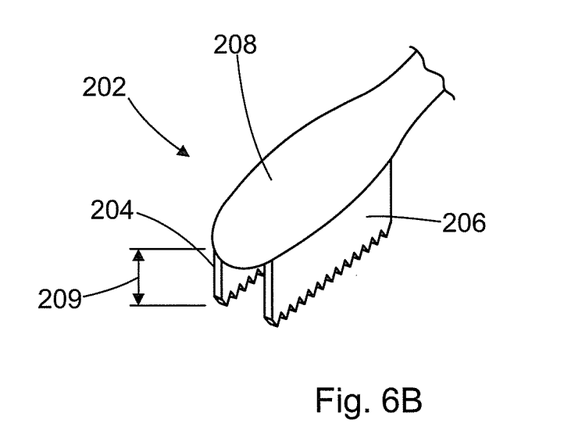
FIG. 6B shows a "toothbrush" saw for use in cutting a keel slot in the tibia.

The surgeon cuts a keel slot in the tibia to accept the keel of the tibial component. A "toothbrush" saw 202, shown in FIG. 6B, is used to do this. It has a pair of parallel blades 204, 206, which extends from the head, referenced 208, of the saw by a predetermined amount 209 designed to suit the keel that is to be used.

In one embodiment, rather than supplying the surgeon with a bespoke prosthetic component, the surgeon may have a kit of parts for knee prosthesis, the kit comprising a plurality of prosthetic components allowing the surgeon to make a choice of which to use based on the individual patient in front of them.

The kit of parts may be arranged so that each component in the kit is intended for use with a patient having a particular value of a given characteristic, or having a value for that given characteristic falling within a predetermined range of values. For example, the characteristic may be height, and each component of the kit may be designed for use with a patient having a height within a particular range. Alternatively, the characteristic might be, for example, anteroposterior length of the tibial plateau, or weight or the patient, BMI of the patient, or other suitable patient parameter.

In such a kit, each tibial component is scaled so that the peripheral thickness is proportional to the desired patient characteristic. For example the thickness of the component might be proportional to patient height.

It can also be convenient to ensure that the length of a component is proportional to the peripheral thickness of the component. For example the components might be arranged so that the ratio of the length of the component to the thickness of the component (i.e. the length divided by the thickness) is a constant (which might be ± an allowable margin of error, such as 0.5 mm, or 0.2 mm or 0.1 mm). In one example kit, the ratio of length to thickness is 20.25 mm±0.2 mm.

Thus a shorter component is also thinner. The correct thickness component for a patient can thus be selected as discussed above, by comparing the length of the tibial components in the kit with a sliver of bone removed from the patient, until the best fit is located.

Other dimensions of the tibial components may also be scaled in a proportional manner. For example, length may be proportional to plate breadth as well as plate thickness.

Length may also (or alternatively) be proportional to keel depth and/or keel length. In one example kit the ratio of length to keel depth (i.e. length divided by keel depth) is 6.75 mm±0.2 mm.

It is preferred that length is proportional to thickness, keel depth, keel length and breadth. An example kit of tibial components might contain six components. The largest component has a known set of dimensions (length, thickness, keel depth, breadth, keel length) and each of the other components has a respective equivalent set of dimensions which is scaled down in proportion to those of the largest component (each dimension being a predetermined percentage of the equivalent dimension of the largest plate, ± an error margin such as 2%, for example). In one example, the smallest component has dimensions approximately 75% of the dimensions of the largest component. The next smallest component has dimensions which are approximately 78% of the dimensions of the largest component. The third smallest component has dimensions which are approximately 84% of the dimensions of the largest component. The third largest component has dimensions which are approximately 90% of the dimensions of the largest component. The second largest component has dimensions which are approximately 95% of the dimensions of the largest component.

In another example kit, the dimensions of the components may vary in proportion to a given dimension of the plate. For example the thickness of the plate may be a predetermined proportion of the plate length (e.g. 5%±2%, or 1%). The depth of the keel may be a predetermined proportion of the plate length (e.g. 15%±2%, or 1%).

Not all the dimensions need vary in proportion. For example, some of the components may share a common keel depth. This might be useful to reduce the number of tools needed by the surgeon.

It will be understood that alterations and modifications can be made to the described embodiments without departing from the scope of the invention as defined herein.

We have stated that the size of smaller tibial implants can be made smaller without increasing the risks of failure of the component beyond an acceptable level. We have some evidence that that is correct where a parametric design is used (i.e. when thickness proportional to length), and where a maximum BMI limit is assumed.

Figure 9:
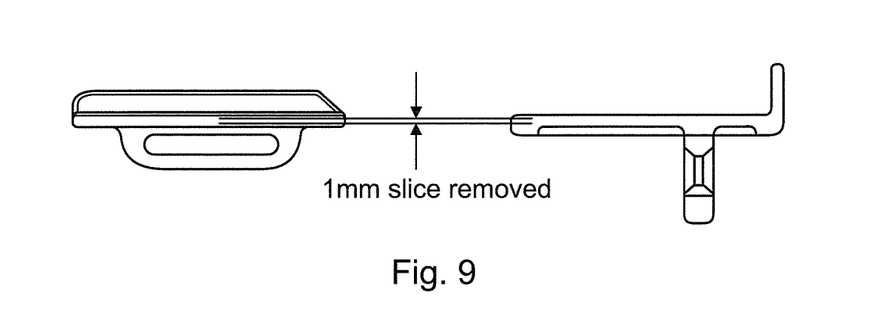
FIG. 9 shows a tibial component having a tibial plate that is 1 mm thinner than the known art.

FIG. 9 shows a tibial component which is more or less the same as prior art tibial components, but with a plate that is 1 mm thinner than before. A 1 mm "slice" of metal has been designed out of the component. Stress analysis on this component indicates that it is strong enough to be used in patients, especially for smaller size components/patients.

Figure 10A:
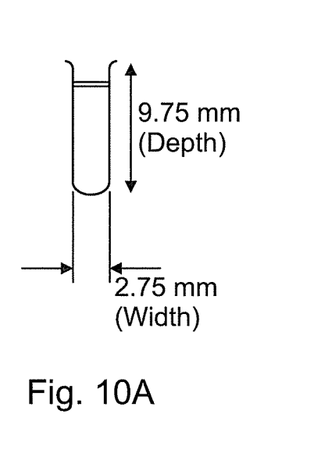
FIGS. 10A and 10B show a comparison between a standard prior art keel and a new keel of reduced depth.
Figure 10B:
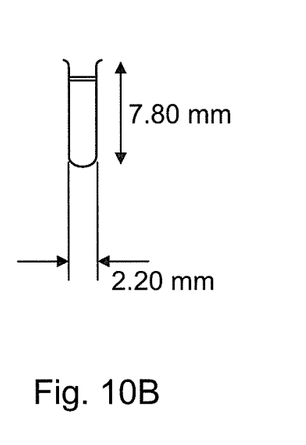

FIGS. 10A and 10B show a standard prior art keel that is 2.7 mm wide and a reduced size keel that is 2.2 mm wide. The central thickness is less than the peripheral thickness to accommodate cement and/or bony ingrowth.

Some embodiments also have reduced keel depth. And some embodiments have the same keel width as before but reduced keel depth. Again, finite element stress analysis has shown these components for smaller people to be generally capable of surviving similar stresses to those experienced by "full-size" components in larger people.

Figure 11:
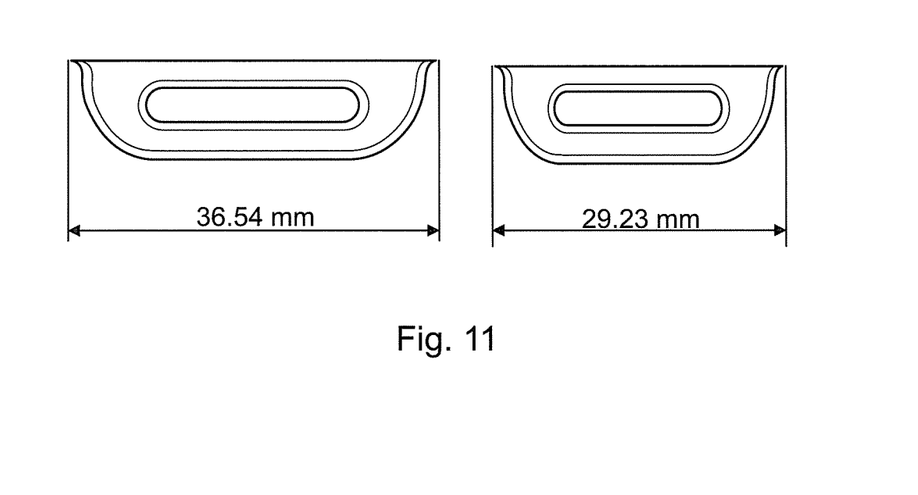
FIG. 11 shows a comparison between the length of a prior art keel on the left and a new keel on the right, for a size C tibial implant.

FIG. 11 shows a prior art full length keel of 36.54 mm and a reduced length keel of 29.23 mm. Again, analysis indicates that the smaller length keel will perform acceptably in smaller patients.

Figure 12:
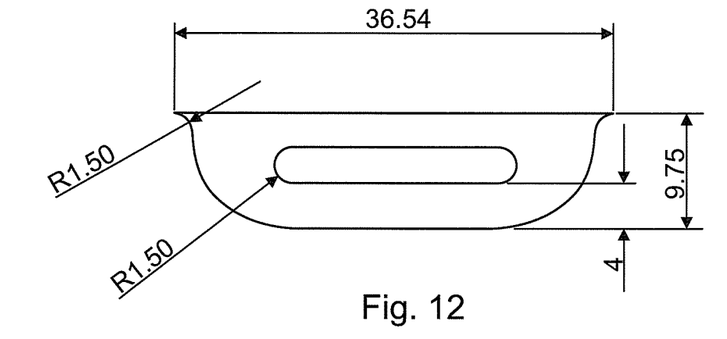
FIGS. 12 and 13 respectively show radiuses of curvature for the prior art keel and a new keel.
Figure 13:
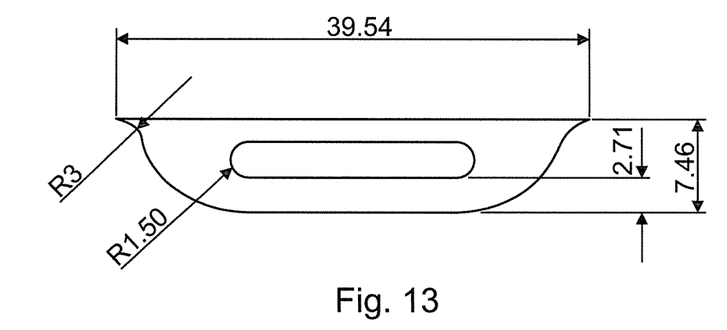

FIGS. 12 and 13 compare a new smaller tibial plate with a prior art tibial plate and indicate a tighter radius of curvature where the keel joins the plate in the smaller plate.

Figure 14:
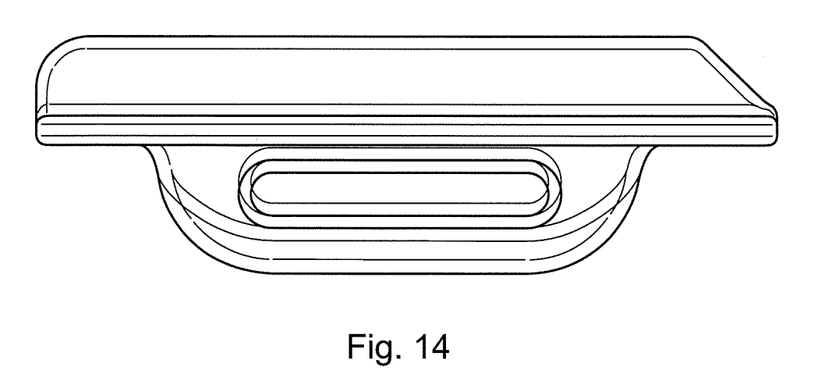
FIG. 14 shows a view of a new keel superimposed on a view of an old keel.

FIG. 14 shows the superposition of a new smaller tibial plate on top of an old larger plate.

Figure 15A:
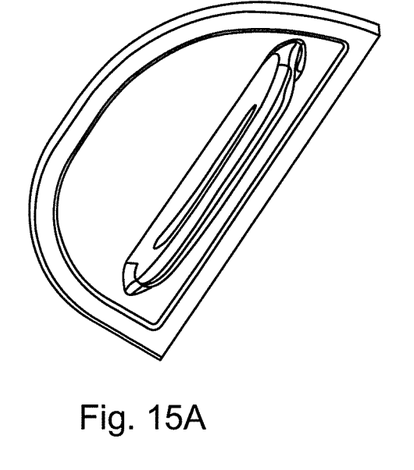
FIGS. 15A and 15B show two new different treatments for the joining of a keel to a tibial plate.
Figure 15B:
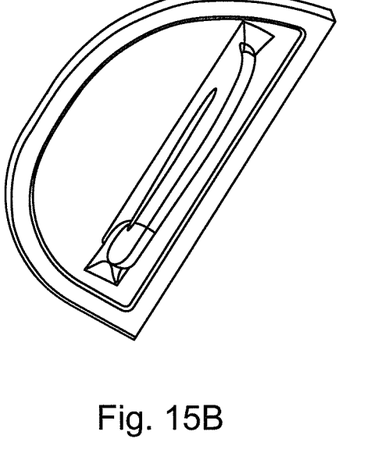

FIGS. 15A and 15B show two ways of treating the fillet where the keel joins the plate. One shows a pointed, tapered join, and the other a flat-faceted wide-nosed join.

It will be appreciated that the invention(s) can be used with both lateral and medial implants.

Figure 16:
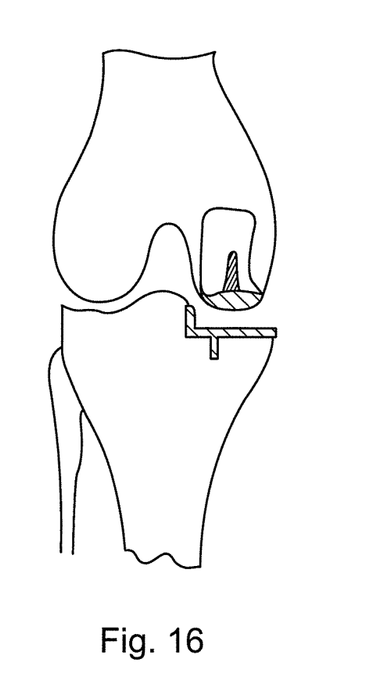
FIGS. 16 and 17 show a medial unicondylar implant.
Figure 17:
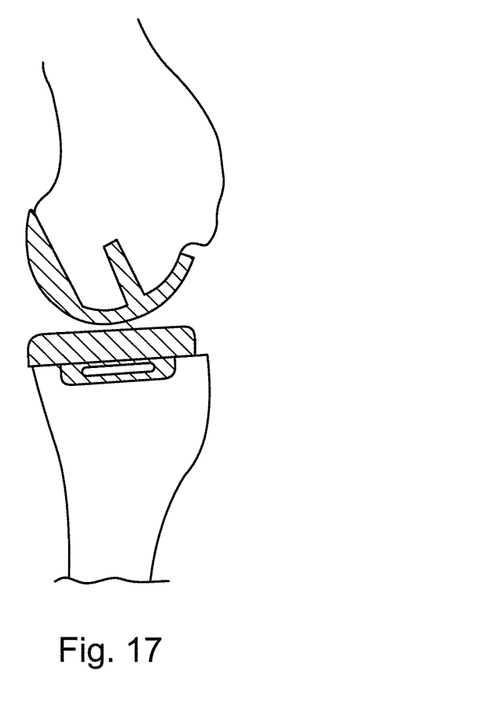

FIGS. 16 and 17 show a tibial implant in accordance with an aspect of the invention used in a medial unicondylar prosthesis. Indeed, statistically more medial replacements are performed than lateral replacements. In FIGS. 16 and 17 no meniscal bearing is shown. It will be appreciated that a meniscal bearing is usually used in combination with the tibial component and femoral component. However, prostheses with no meniscal bearing (but with a tibial component in accordance with aspects of the invention) are potentially envisaged.

It will be appreciated that in the UK and Europe methods of surgery practised on the human or animal body are not patentable as such. However, methods of surgery practised not on "live" patients are patentable. For example methods of practising surgery performed on cadavers or bones (real or artificial) where the aim is not to cure the body. Such methods are intended to be protected.

Moreover, USA and other countries do permit the patenting of methods of surgery practised on patients or animals and protection for these methods is also desired where it is permitted.

It will also be appreciated that in some embodiments the tibial implant will have both a thinner plate and a shallower keel than in the prior art.

Some of the optimal and preferable features of the invention relating to thickness of plate and depth of keel (for example) have been expressed in absolute sizes (e.g. in mm). We may alternatively or additionally want to express them in terms of percentage of the length of the tibial implant, or length of keel. For example thickness of plate and depth of keel that are the same percentage of the length of the implant (or keel) of any of the new implants described or illustrated, plus or minus 1%, or 3%, or 5%, or 10%, or 15%, or 20%. The length of the tibial implants in accordance with the invention and/or keel length, may be the same, or about the same, as the prior art.

The invention claimed is:

1. A method comprising:
 pre-operatively identifying at least one physical attribute of an individual;
 pre-operatively identifying a thickness of a plate based on the at least one physical attribute; and
 providing a tibial prosthetic component comprising the plate having the identified thickness that is less than about 3 mm at a peripheral region of the plate, the plate further includes a length in an antero-posterior direction, and wherein a ratio of the length of the plate to the thickness of the peripheral region is in a range of 20.25±5.

2. The method of claim 1, wherein the at least one physical attribute comprises one or more of: a height of the individual, a weight of the individual, a size of a lateral or medial condyle of a tibia of the individual, a length of the tibia of the individual, a length of a femur of the individual, or a gap between the tibia and the femur of the individual.

3. The method of claim 1, further comprising:
 pre-operatively identifying a depth of a keel on the plate based on the at least one physical attribute.

4. The method of claim 3, wherein:
 a ratio of the length of the plate to the depth of the keel is in a range of 6.75±2.

5. The method of claim 1, wherein the plate is configured to form a tibial plateau of a tibia in the individual.

6. The method of claim 1, wherein providing the tibial prosthetic component comprises selecting the tibial prosthetic component from a system, the system comprising multiple tibial prosthetic components, different ones of the tibial prosthetic components in the system having plates of different thicknesses.

7. A method comprising:
 pre-operatively identifying at least one physical attribute of an individual;
 pre-operatively identifying a keel depth based on the at least one physical attribute; and
 providing a tibial prosthetic component comprising a plate having a keel of the selected keel depth and a length in an antero-posterior direction, and wherein a ratio of the length of the plate to the depth of the keel is in a range of 6.75±2.

8. The method of claim 7, wherein the at least one physical attribute comprises one or more of: a height of the individual, a weight of the individual, a size of a lateral or medial condyle of a tibia of the individual, a length of the tibia of the individual, a length of a femur of the individual, or a gap between the tibia and the femur of the individual.

9. The method of claim 7, further comprising:
 pre-operatively identifying a thickness of the plate based on the at least one physical attribute.

10. The method of claim 7, further comprising at least one of:
 pre-operatively identifying a length of the plate based on the at least one physical attribute; or
 pre-operatively identifying a width of the plate based on the at least one physical attribute.

11. The method of claim 10, wherein at least one of the length of the plate or the width of the plate is proportional to a height of the individual for a given maximum body mass index (BMI).

12. The method of claim 7, wherein an anterior-posterior end of the keel is curved with a radius of curvature of at least about 2 mm.

13. The method of claim 7, wherein providing the tibial prosthetic component comprises selecting the tibial prosthetic component from a system, the system comprising multiple tibial prosthetic components, different ones of the tibial prosthetic components in the system having keels of different keel depths.

14. A method comprising:
 pre-operatively identifying at least one physical attribute of an individual;
 pre-operatively identifying a thickness of a plate based on the at least one physical attribute;
 pre-operatively identifying a keel depth of a keel based on the at least one physical attribute; and
 providing a tibial prosthetic component comprising the plate having the identified thickness, the plate having a keel of the selected keel depth, the tibial prosthetic component selected from a system comprising multiple tibial prosthetic components;
 wherein: the plate is configured to form a tibial plateau of a tibia in the individual,
  there are fewer different keel depths than implant sizes in the system, and
  a first subset of the implant sizes have a common shallower keel depth and a second subset of the implant sizes have a common deeper keel depth.

15. The method of claim 14, wherein different ones of the tibial prosthetic components in the system have plates of different thicknesses.

16. The method of claim 14, wherein different ones of the tibial prosthetic components in the system have keels of different keel depths.

17. The method of claim 14, wherein:
 there are fewer different plate thicknesses than different implant sizes in the kit; and
 a first subset of the implant sizes have a common smaller plate thickness and a second subset of the implant sizes have a common larger plate thickness.

* * * * *